United States Patent
Weissman et al.

(10) Patent No.: US 9,687,509 B2
(45) Date of Patent: Jun. 27, 2017

(54) SILVER OXIDE FORMULATIONS

(75) Inventors: Aharon Weissman, Moreshet (IL);
Perry Antelman, Sharon, MA (US);
Shalom Lampert, Maalot (IL)

(73) Assignee: AIDANCE SKINCARE AND TOPICAL SOLUTIONS, LLC, Woonsocket, RI (US)

(*) Notice: Subject to any disclaimer, the term of this patent is extended or adjusted under 35 U.S.C. 154(b) by 0 days.

(21) Appl. No.: 13/508,373

(22) PCT Filed: Nov. 7, 2010

(86) PCT No.: PCT/US2010/055757
§ 371 (c)(1),
(2), (4) Date: Jun. 25, 2012

(87) PCT Pub. No.: WO2011/057169
PCT Pub. Date: May 12, 2011

(65) Prior Publication Data
US 2012/0276205 A1 Nov. 1, 2012

Related U.S. Application Data

(60) Provisional application No. 61/258,598, filed on Nov. 6, 2009, provisional application No. 61/314,457, filed on Mar. 16, 2010.

(51) Int. Cl.
*A61K 33/38* (2006.01)
*A61L 15/18* (2006.01)
*A61L 15/46* (2006.01)
*A61L 2/232* (2006.01)

(52) U.S. Cl.
CPC .............. *A61K 33/38* (2013.01); *A61L 15/18* (2013.01); *A61L 15/46* (2013.01); *A61L 2/232* (2013.01); *A61L 2300/104* (2013.01); *A61L 2300/404* (2013.01); *A61L 2300/622* (2013.01); *Y10T 428/2982* (2015.01)

(58) Field of Classification Search
CPC .......... A61K 33/38; A61K 47/02; A61K 8/19; A61K 9/0014; A61K 9/14; A61L 15/18; A61L 2300/104; A61L 2300/63
See application file for complete search history.

(56) References Cited

U.S. PATENT DOCUMENTS

| | | | | |
|---|---|---|---|---|
| 4,360,387 A | * | 11/1982 | Brown et al. | 106/243 |
| 5,098,582 A | * | 3/1992 | Antelman | 210/759 |
| 5,336,499 A | * | 8/1994 | Antelman | 424/405 |
| 5,676,977 A | * | 10/1997 | Antelman | 424/618 |
| 2006/0171971 A1 | | 8/2006 | Marsh et al. | |
| 2006/0210500 A1 | | 9/2006 | Bicard-Benhamou et al. | |
| 2008/0050452 A1 | | 2/2008 | Chen et al. | |
| 2008/0181951 A1 | * | 7/2008 | Holladay et al. | 424/485 |
| 2010/0196515 A1 | | 8/2010 | Kamiya et al. | |
| 2011/0020468 A1 | * | 1/2011 | Antelman | 424/618 |

OTHER PUBLICATIONS

Dellasega et al (Nanostructured high valence silver oxide produced by pulsed laser deposition, online on Aug. 6, 2008, Applied Surface Science, vol. 255, pp. 5248-5251).*
American Elements website (Silver Oxide Powder, Jul. 18, 2008 on Wayback Machine).*
American Elements (Silver Oxide Powder, http://www.americanelements.com/agoxp.html, Wayback machine date of Aug. 9, 2007).*
Waterhouse et al (Physical Chemistry Chemical Physics, Jan. 2001, pp. 3838-3845).*
Waterhouse et al., "The Thermal Decomposition of Silver (I,III) oxide: A combined XRD, FT-IR and Raman spectroscopic study", Physical Chemistry Chemical Physics—Jan. 2001.

* cited by examiner

*Primary Examiner* — Mark V Stevens
(74) *Attorney, Agent, or Firm* — Daniel Feigelson; Fourth Dimension IP

(57) ABSTRACT

A formulation including at least one silver oxide including a silver(II) oxide, the silver(II) oxide having an irregular macrocrystal structure, the silver oxide having an average particle size ($D_{50}$) below 8 micrometers, the irregular macrocrystal structure characterized by a diffraction peak in a {111} diffraction plane having at least one of the following structural properties: (i) a measured full width half maximum (FWHM) of the peak being at least 0.24 degrees of $2\theta$; and (ii) a net full width half maximum (net FWHM) of the peak being at least 0.14 degrees of $2\theta$.

19 Claims, 10 Drawing Sheets

| 2-Theta | d(Å) | BG | Height | H% | Area | A% | FWHM | XS(Å) |
|---|---|---|---|---|---|---|---|---|
| 15.854 | 5.5856 | 11.3 | 21.7 | 2.3 | 4.1 | 1.9 | 0.162 | 793 |
| 30.182 | 2.9687 | 7.3 | 21.7 | 2.3 | 4.1 | 1.9 | 0.161 | 690 |
| 32.039 | 2.7913 | 12.0 | 446.0 | 47.3 | 129.0 | 59.5 | 0.246 | 392 |
| 32.261 | 2.7726 | 12.1 | 941.9 | 100.0 | 216.8 | 100.0 | 0.196 | 523 |
| 34.177 | 2.6214 | 12.6 | 305.4 | 32.4 | 61.4 | 28.3 | 0.171 | 625 |
| 37.144 | 2.4185 | 10.2 | 739.8 | 78.5 | 165.6 | 76.4 | 0.190 | 538 |
| 39.383 | 2.2860 | 6.0 | 287.0 | 30.5 | 72.0 | 33.2 | 0.213 | 465 |
| 52.477 | 1.7423 | 7.2 | 74.8 | 7.9 | 19.6 | 9.0 | 0.223 | 454 |
| 53.858 | 1.7008 | 10.5 | 175.5 | 18.6 | 44.8 | 20.7 | 0.217 | 470 |
| 54.682 | 1.6772 | 11.3 | 104.7 | 11.1 | 24.9 | 11.5 | 0.202 | 513 |
| 56.700 | 1.6222 | 7.6 | 167.4 | 17.8 | 38.1 | 17.6 | 0.193 | 548 |
| 62.781 | 1.4789 | 12.4 | 96.6 | 10.3 | 23.7 | 10.9 | 0.209 | 516 |
| 63.656 | 1.4606 | 15.4 | 76.6 | 8.1 | 24.4 | 11.2 | 0.270 | 383 |
| 64.124 | 1.4511 | 13.2 | 88.8 | 9.4 | 25.9 | 12.0 | 0.248 | 424 |
| 65.561 | 1.4227 | 8.4 | 36.6 | 3.9 | 13.4 | 6.2 | 0.312 | 329 |
| 66.240 | 1.4098 | 8.7 | 61.3 | 6.5 | 23.1 | 10.7 | 0.321 | 321 |
| 66.960 | 1.3964 | 13.1 | 83.9 | 8.9 | 28.1 | 13.0 | 0.285 | 369 |
| 67.560 | 1.3854 | 6.1 | 62.9 | 6.7 | 26.4 | 12.2 | 0.358 | 287 |
| 69.379 | 1.3535 | 5.7 | 31.3 | 3.3 | 8.8 | 4.0 | 0.238 | 462 |
| 71.980 | 1.3108 | 4.7 | 32.3 | 3.4 | 10.3 | 4.7 | 0.270 | 406 |
| 79.252 | 1.2078 | 3.9 | 43.1 | 4.6 | 12.3 | 5.7 | 0.242 | 496 |

SILVER OXIDE FORMULATIONS

This application draws priority from U.S. Provisional Patent Application Ser. No. 61/258,598, filed Nov. 6, 2009, and from U.S. Provisional Patent Application Ser. No. 61/314,457, filed Mar. 16, 2010, both of which are incorporated by reference for all purposes as if fully set forth herein.

FIELD AND BACKGROUND OF THE INVENTION

The present invention relates to anti-microbial silver oxide formulations.

Silver and silver derivatives are known to have anti-microbial properties. Commercial applications of such products include impregnated bandages, mold-free and odor-free textiles, and various kinds of skin creams. In addition, there exist several oral medicines that utilize silver as an active ingredient, including anti-smoking lozenges containing silver acetate ($AgC_2H_3O_2$), breath mints coated with silver, and silver nitrate solutions for treating gum disease.

One particularly effective group of silver derivatives is the group of silver oxides. Of the oxides, AgO is known to be more effective than $Ag_2O$.

It was reported by U.S. Pat. No. 6,258,385 to Antelman, which is incorporated by reference for all purposes as if fully set forth herein, that the effects of the electron transfer involved with respect to the tetroxide, phenomenally, rendered it a more powerful germicide than other silver entities . . . . The oligodynamic properties of these entities may be summarized as follows, which is referred to as the Horsfal series:

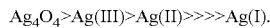

$Ag_4O_4 > Ag(III) > Ag(II) \ggg Ag(I)$.

The advances in anti-microbial silver oxide formulations notwithstanding, it is believed that there is a need for further improvements in such formulations, and the subject matter of the present disclosure and claims is aimed at fulfilling this need.

SUMMARY OF THE INVENTION

According to the teachings of the present invention there is provided a formulation including at least one silver oxide including a silver(II) oxide, the silver(II) oxide having an irregular macrocrystal structure, the silver oxide having an average particle size ($D_{50}$) below 8 micrometers, the irregular macrocrystal structure characterized by a diffraction peak in a {111} diffraction plane having at least one of the following structural properties: (i) a measured full width half maximum (FWHM) of the peak of at least 0.24 degrees of $2\theta$; and (ii) a net full width half maximum (net FWHM) of the peak of at least 0.14 degrees of $2\theta$.

According to another aspect of the present invention there is provided a formulation including a solid phase containing at least one silver oxide including a silver(II) oxide, the silver(II) oxide having an irregular macrocrystal structure, the silver oxide having an average particle size ($D_{50}$) below 8 micrometers, wherein the irregular macrocrystal structure is structurally characterized by a lability pattern of a thermogravimetric analysis (TGA) performed on the solid phase in a chamber, under a pure nitrogen environment and a temperature ramp rate of 10° C./minute, the lability pattern being characteristic of structural properties within the irregular macrocrystal structure, the lability pattern having at least one of the following properties: (i) a derivative of weight loss of the solid phase with respect to a temperature change in the chamber peaks at a temperature below 202° C.; and (ii) a first shoulder of the derivative appears below 165° C.

According to yet another aspect of the present invention there is provided a formulation including at least one silver oxide including a silver(II) oxide, the silver oxide having an average particle size within a range of 0.8 micrometers and 4.5 micrometers.

According to further features in the described preferred embodiments, the formulation is a topical formulation for application to skin tissue, wherein, within the topical formulation, the silver oxide is dispersed or intimately dispersed in a base material.

According to still further features in the described preferred embodiments, the silver oxide includes silver(I) oxide, and wherein a ratio of the silver(I) oxide to the silver(II) oxide is at least 0.05:1, at least 0.06:1, at least 0.07:1, at least 0.08:1, at least 0.10:1, at least 0.15:1, or at least 0.20:1, by weight.

According to still further features in the described preferred embodiments, the silver oxide has an average particle size within a range of 0.8 micrometers and 4.5 micrometers.

According to still further features in the described preferred embodiments, the silver oxide has an average particle size above 0.8 micrometers, above 0.9 micrometers, above 1.0 micrometer, above 1.2 micrometers, or above 1.5 micrometers.

According to still further features in the described preferred embodiments, the formulation contains at least 0.05%, at least 0.10%, at least 0.15%, at least 0.25%, or at least 0.50%, by weight, of the silver(II) oxide.

According to still further features in the described preferred embodiments, the silver oxide has an average particle size ($D_{50}$) below 4.5 micrometers, below 4 micrometers, below 3 micrometers, below 2.5 micrometers, or below 2.0 micrometers.

According to still further features in the described preferred embodiments, the silver oxide largely includes or predominantly includes the silver(II) oxide.

According to still further features in the described preferred embodiments, the silver(II) oxide includes, largely includes, or consists substantially of tetrasilver tetroxide.

According to still further features in the described preferred embodiments, the diffraction peak is characterized by the $2\theta$ being within at least one of a range of 37-37.5 degrees, and a range of 37.1-37.4 degrees.

According to still further features in the described preferred embodiments, the base material includes a liquid wax ester.

According to still further features in the described preferred embodiments, the base material includes at least one wax.

According to still further features in the described preferred embodiments, the at least one wax includes a solid wax that is solid at a temperature of 20° C.

According to still further features in the described preferred embodiments, the formulation further includes a solid wax ester.

According to still further features in the described preferred embodiments, the liquid wax ester has an average carbon number of up to 46, up to 44, or up to 42.

According to still further features in the described preferred embodiments, the liquid wax ester has an average carbon number of at least 34, at least 36, or at least 38.

According to still further features in the described preferred embodiments, the liquid wax ester includes jojoba oil.

According to still further features in the described preferred embodiments, the solid wax ester includes hydrogenated jojoba oil.

According to still further features in the described preferred embodiments, the silver oxide includes a silver(I) oxide, and wherein the ratio of the silver(I) oxide to the silver(II) oxide is less than 5:1, less than 2:1, less than 1:1, less than 0.8:1, or less than 0.5:1, by weight.

According to still further features in the described preferred embodiments, the measured full width half maximum (FWHM) is at least 0.24 degrees, at least 0.25 degrees, at least 0.28 degrees, at least 0.30 degrees, at least 0.32 degrees, or at least 0.35 degrees of 2θ.

According to still further features in the described preferred embodiments, the net full width half maximum (FWHM) is at least 0.14 degrees, at least 0.15 degrees, at least 0.16 degrees, at least 0.18 degrees, at least 0.20 degrees, at least 0.22 degrees, or at least 0.25 degrees, of 2θ.

According to still further features in the described preferred embodiments, the irregular macrocrystal structure is structurally characterized by a lability pattern of a thermogravimetric analysis (TGA) performed on the solid phase in a chamber, under a pure nitrogen environment and a temperature ramp rate of 10° C./minute, and wherein a derivative of weight loss of the solid phase with respect to a temperature change in the chamber peaks at a temperature below 202° C., below 200° C., below 198° C., below 197° C., or below 195° C.

According to still further features in the described preferred embodiments, the irregular macrocrystal structure is structurally characterized by a lability pattern of a thermogravimetric analysis (TGA) performed on the solid phase in a chamber, under a pure nitrogen environment and a temperature ramp rate of 10° C./minute, and wherein a first shoulder of a derivative of weight loss of the solid phase with respect to a temperature change in the chamber appears below 165° C., below 160° C., below 155° C., or below 150° C.

According to still further features in the described preferred embodiments, the derivative peaks at a temperature below 200° C., below 198° C., below 197° C., or below 195° C.

According to still further features in the described preferred embodiments, a first shoulder of the derivative appears below 160° C., below 155° C., or below 150° C.

According to still further features in the described preferred embodiments, the carrier base includes a solid wax such as a beeswax.

According to still further features in the described preferred embodiments, the carrier base includes water.

According to further teachings of the present invention there is provided a wound dressing including any of the formulations described herein.

According to still further features in the described preferred embodiments, the wound dressing includes an adhesive-containing bandage, a cotton roll bandage, or a gelable polymer.

According to further teachings of the present invention there is provided a medical device including an ointment or oil-based cream according to any of the formulations described herein.

According to further teachings of the present invention there is provided a medical device including an emulsion according to any of the formulations described herein.

According to further teachings of the present invention there is provided a medical device including a water-based cream according to any of the formulations described herein.

According to yet another aspect of the present invention there is provided a method including the steps of: (a) providing a formulation, medical device, or wound dressing, including any of those recited by of any one of the above claims, and (b) applying the composition, formulation, medical device, or wound dressing to skin tissue.

According to still further features in the described preferred embodiments, the formulation, medical device, or wound dressing is applied to the skin tissue to effect a treatment of the skin tissue.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings.

DESCRIPTION OF THE PREFERRED EMBODIMENTS

Figure 1:
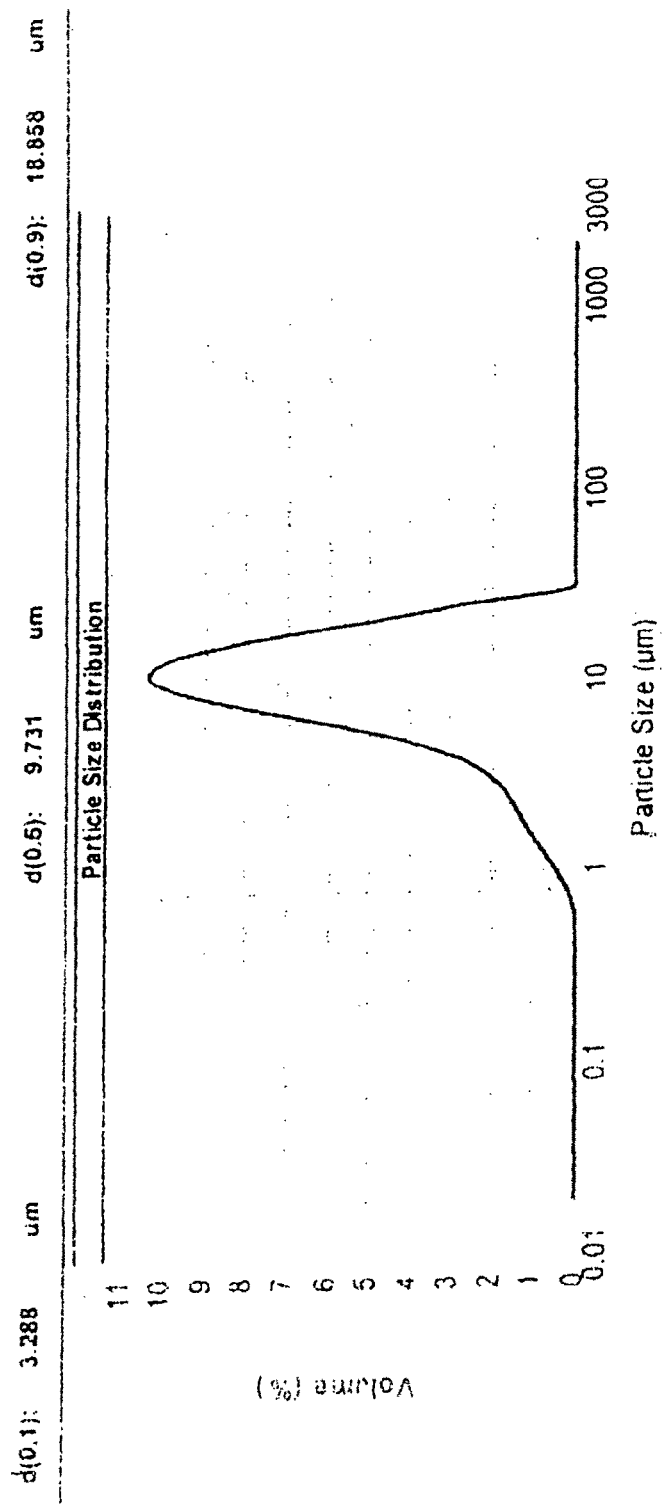
FIG. 1 is a graphical representation of a differential Particle Size Distribution (PSD) of an unmilled silver oxide sample.

Before explaining at least one embodiment of the invention in detail, it is to be understood that the invention is not limited in its application to the details set forth in the following description. The invention may be capable of other embodiments or of being practiced or carried out in various ways. Also, it is to be understood that the phraseology and terminology employed herein is for the purpose of description and should not be regarded as limiting.

We have discovered that a mixture of silver(II) oxide and silver(I) oxide may be appreciably more efficacious than is indicated by the Horsfal series provided hereinabove.

We have further discovered that under certain physical processing conditions, silver(II) oxide may be surprisingly converted to silver(I) oxide. In the conversion process, oxygen may be liberated, and/or a silver(III) oxide may be formed.

We have also discovered that under certain physical processing conditions, described hereinbelow, crystalline silver(II) oxide may be surprisingly converted to a semi-crystalline, irregular, and/or possibly amorphous silver oxide.

Thus, one aspect of the present invention relates to a silver-oxide based formulation or medical device that may be particularly efficacious in various bacteriostatic or bacteriocidal applications. Such formulations or medical devices may be efficacious in the inhibition, treatment and cure of various medical conditions, and in particular, dermatological conditions. The formulation or medical device may include a mixture of silver(II) oxide and silver(I) oxide, and/or a mixture of a crystalline silver(II) oxide and a silver oxide having a low degree of crystallinity.

An exemplary general procedure for producing oil-based silver(II) oxide formulations according to the present invention is as follows: an oil such as jojoba oil is heated, preferably to around 80° C. A wax such as beeswax may be melted into the oil. The material may be mixed thoroughly as it is cooled, typically below about 60° C. Optionally, an essential oil such as palmarosa oil may be added. Mixing may be continued as the fine silver oxide material is introduced, and further mixing may ensue, typically for 0.5 to 2 hours, during cooling of the mixture to below about 40° C. The formulation may then be poured into storage containers.

Typically, the formulations contain a total silver(II) oxide content of at least 0.01% or 0.02%, by weight, more typically, 0.05% to 3%, by weight, and yet more typically, 0.1% to 3% silver oxide. The silver oxide may predominantly consist of tetrasilver tetroxide ($Ag_4O_4$), or AgO.

Alternatively, water-based formulations or emulsion-based formulations may be produced. These formulations may typically contain 50-99% water, 0.5% to 30% of a thickening agent and/or an emulsifier, up to 60% jojoba oil, typically clear jojoba oil (usually 1-60%), and between 0.01% and 3% silver(II) oxide. Various clays, including members of the smectite family such as bentonite, may be used as the thickening agent.

The inventive materials may be incorporated in a medical device that may be particularly efficacious in various bacteriostatic or bacteriocidal applications. These applications may include the inhibition, treatment and cure of various medical conditions, such as dermatological conditions.

EXAMPLES

Reference is now made to the following examples, which together with the above description, illustrate the invention in a non-limiting fashion.

Example 1

The performance of the unmilled, silver(II) oxide raw material having an average particle size above 5 microm-eters, and typically, between 10 and 15 micrometers, was evaluated, in a series of in-vitro tests, against the performance of the milled material having an average particle size between 1 and 5 micrometers. The tests were conducted using cultures containing one of five different microorganisms: *Staphylococcus aureus, Bacillus subtilis, Pseudomonas aeruginosa, Candida albicans*, and *Aspergillus niger*, at least some of which may play an important role in various dermatological conditions, including infections.

In the case of *Aspergillus niger*, no substantial difference in performance was observed. Using *Staphylococcus aureus, Bacillus subtilis, Pseudomonas aeruginosa*, and *Candida albicans*, however, the milled silver(II) oxide of the present invention exhibited a higher efficacy.

Example 2

The exemplary raw materials were crystalline, partially agglomerated silver(II) oxide having a chemical purity of between about 95.5 and 97% and an average particle size (D50) of at least 5 micrometers, and typically, approximately 10 to 20 micrometers, as determined by laser diffraction particle size analysis (Mastersizer™ 2000 of Malvern Instruments, England; Microtrac 53500, USA).

The raw materials were milled in a vortex mill (Superfine Inc., Israel) in a nitrogen-rich environment, to produce a fine silver oxide powder in which much of the agglomerated material has been comminuted. The specific energy applied during the milling process was typically between 6 and 30 kilojoules per kilogram (or kilowatt·second per kilogram), and more typically, between 8 and 25 kilojoules per kilogram. Typically, the milled product had an average particle size that was smaller by at least one micrometer with respect to the average particle size of the unmilled material from which it was produced. More typically, the milled product was smaller by at least 1.2 micrometers, by at least 1.5 micrometers, by at least 2 micrometers, by at least 3 micrometers, or by at least 5 micrometers or by at least 7 micrometers. In most cases, the average particle size was reduced by at least 30%, at least 40%, at least 50%, at least 60%, or at least 80%.

The average particle size of the milled material was above about 0.8 micrometers above about 0.9 micrometers, and more typically, above about 1 micrometer, above about 1.3 micrometers, or above about 1.7 micrometers.

Example 3

The raw materials and the inventive processed powders of Example 2 were subjected to X-ray diffraction. Under the processing conditions of Example 2, we discovered that a portion of the raw material was converted to a crystalline silver(I) oxide ($Ag_2O$), possibly by a mechano-chemical reaction. Using quantitative X-ray diffraction methods, the fraction of crystalline silver(I) oxide in the product material was determined to be higher than the fraction pre-existing in the raw materials. The quantitative X-ray diffraction methods used were found to be insensitive for measuring absolute silver(I) oxide contents below about 3% to 5%. A more accurate quantitative analysis for measuring silver(I) oxide content in a mixed silver oxide environment is provided hereinbelow.

From a quantitative standpoint, the fraction of crystalline silver(I) oxide in the product material was determined to be higher than the fraction pre-existing in the raw materials by at least 1.5%, at least 2%, at least 3%, or at least 4%. In some cases, the fraction of crystalline silver(I) oxide in the product material was determined to be higher than the fraction pre-existing in the raw materials by at least 6%, at least 10%, or at least 15%, by weight.

In absolute terms, the fraction of crystalline silver(I) oxide in the vortex-milled product material was at least 5%, at least 6%, at least 7%, at least 8%, or at least 10%. As is evident from Tables 1 and 2, the fraction of crystalline silver (I) oxide in the product material was, in some cases, at least 20%, at least 23%, or at least 25%, by weight.

TABLE 1

| | $D_{50}$ (micrometers) | $Ag_2O$ content (% w/w) | Description |
|---|---|---|---|
| Sample 1 | 5 | 5> | Unmilled |
| Sample 2 | 2.25 | 14 | Milled according to Example 2 |
| Sample 3 | 1.17 | 23 | Milled according to Example 2 |

TABLE 2

| | $D_{50}$ (micrometers) | $Ag_2O$ content (% w/w) | Description |
|---|---|---|---|
| Sample 4 | 15 | 5> | Unmilled |
| Sample 5 | 2.7 | 27 | Milled according to Example 2 |
| Sample 6 | 2.8 | 31 | Milled according to Example 2 |
| Sample 7 | 3.5 | 19 | Milled according to Example 2 |

We have further discovered that under particular processing conditions, including those described in Example 1, a semi-crystalline or at least partially amorphous silver oxide material may be produced from crystalline silver(II) oxide. At present, we believe that this material may be a semi-crystalline silver(II) oxide. It may be possible that some semi-crystalline silver(III) oxide such as $Ag_2O_3$ is also produced. The production of a semi-crystalline silver(III) oxide may be indicated by the formation of silver(I) oxide described hereinabove, according to the following exemplary reaction:

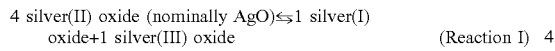

4 silver(II) oxide (nominally AgO)⇌1 silver(I) oxide+1 silver(III) oxide     (Reaction I)

Alternatively or additionally, oxygen may be liberated, according to the following exemplary reaction:

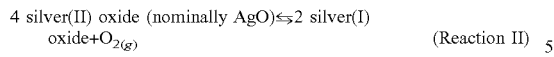

4 silver(II) oxide (nominally AgO)⇌2 silver(I) oxide+$O_{2(g)}$     (Reaction II)

However, evidence for the formation of silver(III) oxide remains to be positively demonstrated.

The ratio of silver(I) oxide to silver(II) oxide (or the ratio of substantially crystalline silver(I) oxide to substantially crystalline silver(II) oxide) may exceed about 1:20, 1:18, 1:16, or 1:10, by weight. Typically, the ratio of the silver(I) oxide to the silver(II) oxide (or the ratio of substantially crystalline silver(I) oxide to substantially crystalline silver (II) oxide) may be less than 5:1, less than 2:1, less than 1:1, less than 0.8:1, or less than 0.5:1, by weight. Without wishing to be bound by theory, we believe that this ratio (specifying the relative quantity of silver oxide that is not fully crystalline) may be somewhat dependent on the specific energy applied during the milling process.

It is possible that some of the semi-crystalline material produced is a silver(II) oxide characterized by a low level of crystallinity. This may be supported by the broadening of various X-ray diffraction peaks associated with crystalline silver(II) oxide. For example, Table 3 provides the characteristic of a given diffraction line (2θ=37.23° in the {111} diffraction or symmetry plane) appearing in both the raw material and in milled samples. The comparison refers to the peak heights and full width half maximums (FWHMs). A standard sample containing well-crystallized Si crystals, displayed a FWHM of 0.08°, which may represent the natural line broadening of the diffractometer. Sample 1, consisting of unmilled silver oxide, yielded a FWHM of 0.207°. Samples 2 and 3, which were milled from Sample 1, exhibited broadened peaks having significantly increased FWHMs, 0.355° and 0.446°, respectively. The net broadening, after subtracting the instrumental broadening, is 0.127 for Sample 1, and 0.275 and 0.366, respectively, for vortex-milled Samples 2 and 3, respectively.

Thus, under the specific experimental conditions, the processed powders appear to have undergone a mechano-chemical reaction in two stages. In the first stage, strains are introduced into the structure of the crystals, increasing the irregularity of the lattice structure, i.e., the disarray in the location of the atoms within the lattice structure. In the second stage, a chemical reaction takes place, leading to a partial chemical decomposition of the crystals and the formation of new phases such as silver(I) oxide ($Ag_2O$). Thus, the two-stage mechano-chemical reaction yields a silver(II) oxide lattice structure having a low level of crystallinity, along with at least one additional phase of silver oxide such as silver(I) oxide.

Since the milling process effects changes in the macrostructure of the crystals (i.e., on the order of 1 micrometer), the crystallite size may be substantially unchanged. Hence, the broadening of a diffraction peak associated with crystalline silver(II) oxide may characterize the strain introduced to the crystals during the milling. Alternatively, from the broadening of a peak associated with crystalline silver(II) oxide, the strain introduced to the crystals during the milling process may be calculated.

TABLE 3

| | $D_{50}$ (micrometers) | Peak Height (cps) | Peak full width half maximum (° of 2θ) | Description |
|---|---|---|---|---|
| Sample 1 | 5 | 899 | 0.207 | Unmilled |
| Sample 2 | 2.25 | 438 | 0.355 | Milled according to Example 2 |
| Sample 3 | 1.17 | 255 | 0.446 | Milled according to Example 2 |
| Standard | ~1.0 | 9377 | 0.08 | Si standard - fully crystalline |

Example 4

The specific surface area of various silver oxide samples was determined using a BET procedure, under nitrogen. The results are provided in Table 4.

TABLE 4

| | $D_{50}$ (micrometers) | Specific Surface Area ($m^2/g$) |
|---|---|---|
| Sample 4 | 15 | 0.96 |
| Sample 7 | 3.5 | 1.05 |
| Sample 5 | 2.65 | 1.23 |

The processed mixtures of silver oxides and formulations containing such mixtures, may be appreciably more efficacious than the unprocessed silver(II) oxide raw material. As is evident from Table 4, however, the specific surface area of the inventive materials is only about 10-25% higher than that of the raw material. Consequently, it would appear that the improved efficacy may not be attributable to, or at most, may be only partially attributable to, the very moderate increased specific surface area of the inventive mixed silver oxide materials.

Example 5

To a stirred vessel were introduced 600 grams of water and 240 grams of clear jojoba oil. Subsequently, 50 grams of bentonite and 0.9 grams of silver(II) oxide were introduced, and stirring was continued until a viscous emulsion was produced.

Example 6

To a stirred vessel were introduced 600 grams of water and 10 grams of clear jojoba oil. Subsequently, 50 grams of bentonite and 9.0 grams of silver(II) oxide were introduced, and stirring was continued until a single-phase, water-based cream was produced.

Example 7

Crystalline, partially agglomerated tetrasilver tetroxide (Sample 8), a form of silver(II) oxide, was milled in a vortex mill substantially as described in Example 2. The average particle size ($D_{50}$) of the unmilled raw material was 9.7 micrometers ($\mu$), as determined by laser diffraction particle size analysis (also as above).

After vortex milling, a first portion of the milled material (Sample 9) was characterized, and a second portion was remilled (Sample 10) and then characterized.

Figure 2:
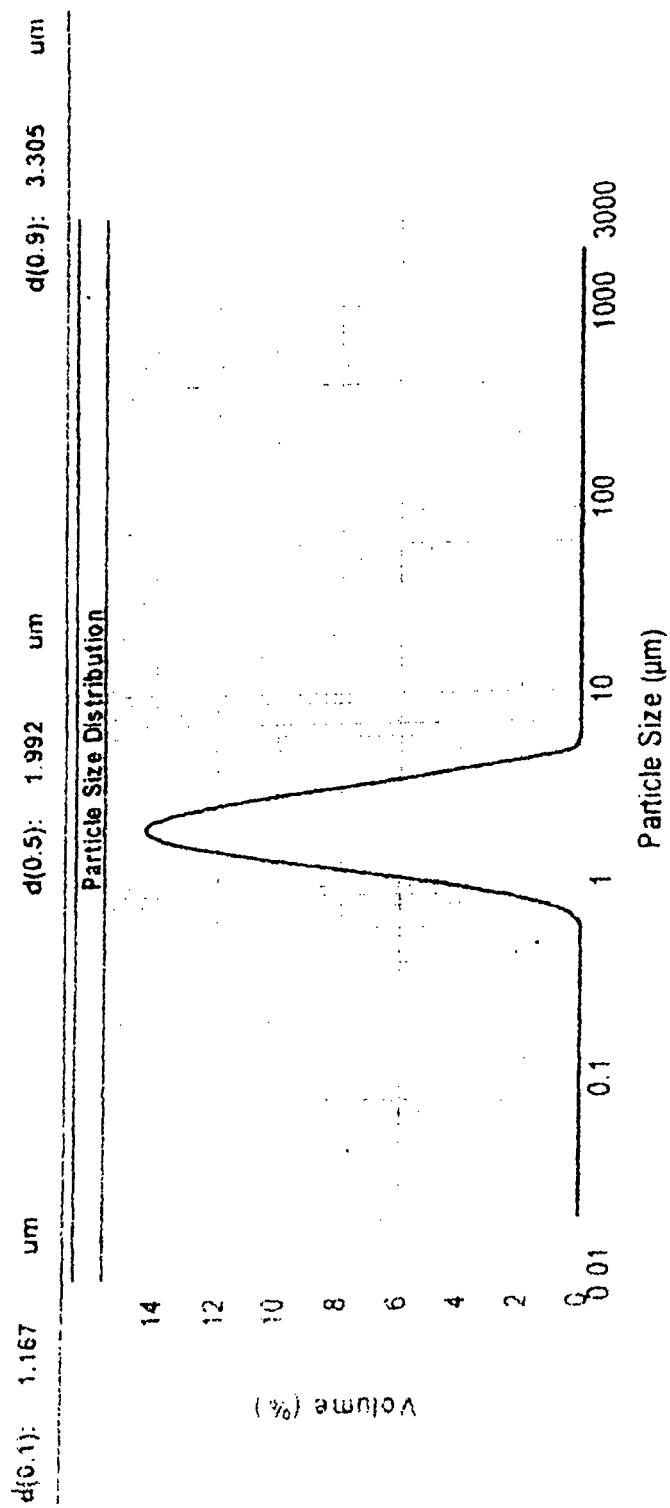
FIG. 2 is a graphical representation of a differential PSD of an inventive silver oxide material produced by a first milling operation in a vortex mill.
Figure 3:
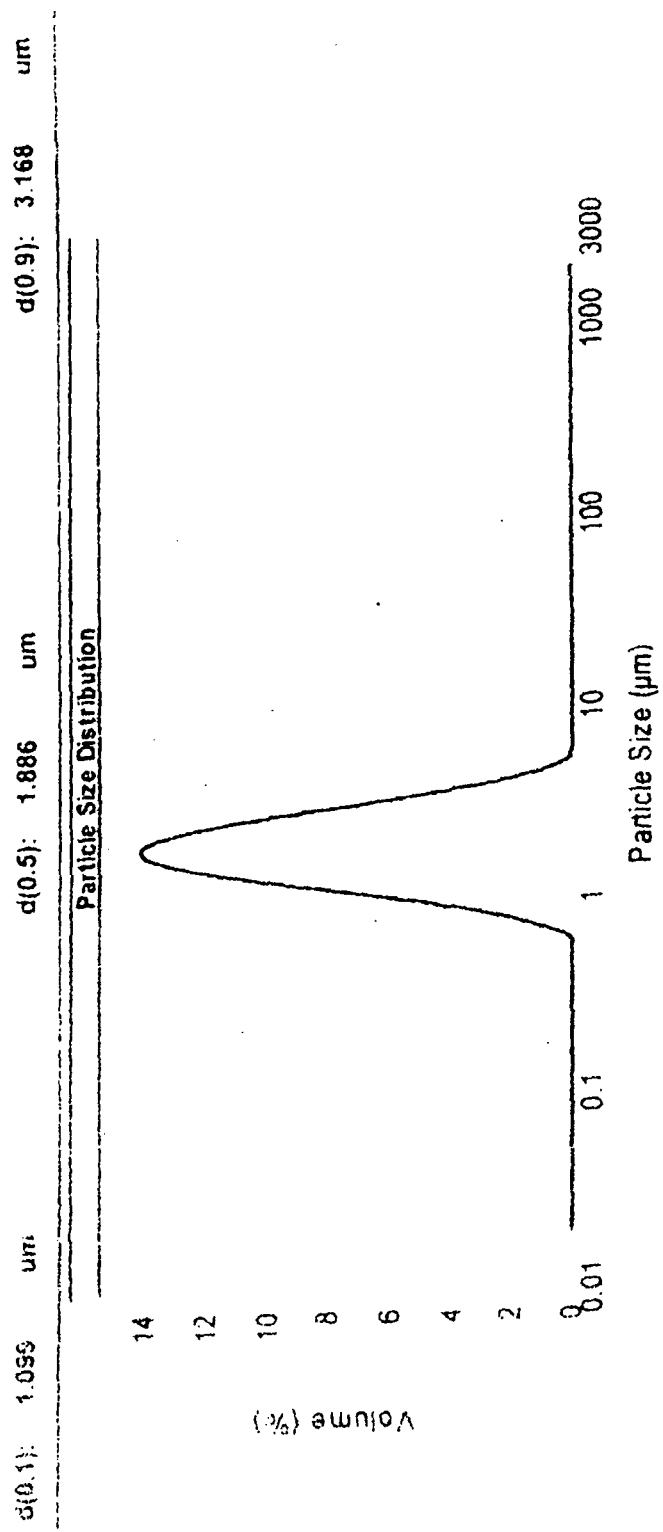
FIG. 3 is a graphical representation of a differential PSD of an inventive silver oxide material produced by vortex-milling the inventive silver oxide sample associated with FIG. 2.

Particle size distributions (PSDs) of the unmilled raw material and of the two milled samples are provided in Table 5. A substantially differential PSD, in which volume percent is plotted as a function of particle size, is provided for each of the three samples in FIGS. 1-3, respectively.

TABLE 5

|  | $D_{10}$ ($\mu$) | $D_{50}$ ($\mu$) | $D_{90}$ ($\mu$) | $D_{100}$ ($\mu$) | Description |
|---|---|---|---|---|---|
| Sample 8 | 3.3 | 9.7 | 18.9 | ~30 | Unmilled |
| Sample 9 | 1.1 | 2.0 | 3.3 | ~5.8 | Milled according to Example 2 |
| Sample 10 | 1.1 | 1.9 | 3.2 | ~5.8 | Milled according to Example 2 |

It is evident from Table 5 that the PSD of Sample 10, produced by the additional milling procedure, is extremely similar to the PSD of Sample 9, which had been previously milled.

Example 8

Material from Samples 8-10 were subjected to X-ray diffraction (XRD), using a Rigaku Dmax 2000 XRD analyzer (Rigaku Corporation, Japan).

Figure 4:
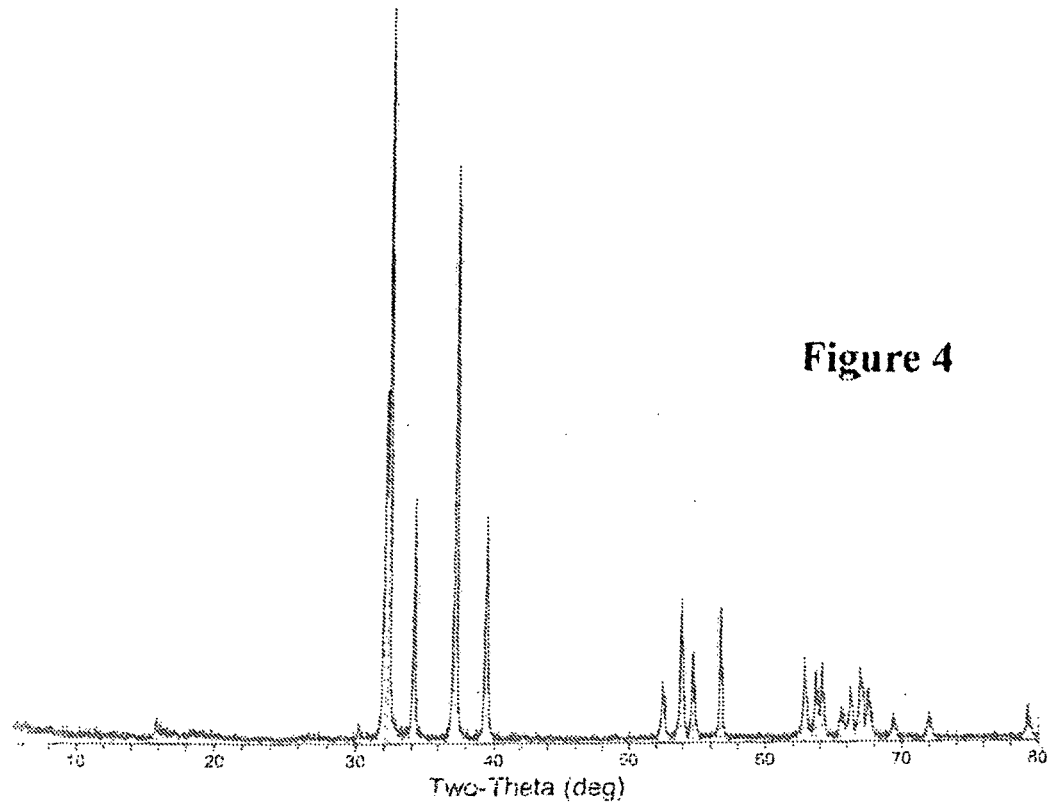
FIG. 4 is an X-ray diffraction plot of the unmilled silver oxide sample associated with FIG. 1.
Figure 5:
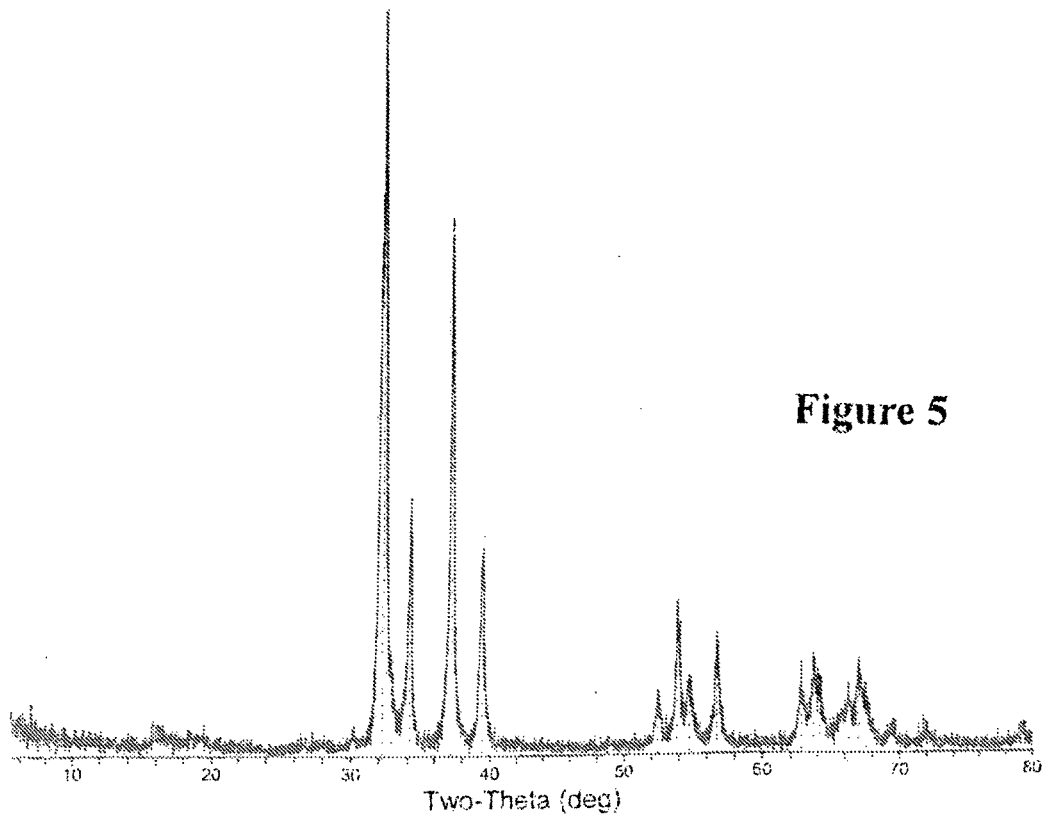
FIG. 5 is an X-ray diffraction plot of the milled silver oxide sample associated with FIG. 2.
Figure 6:
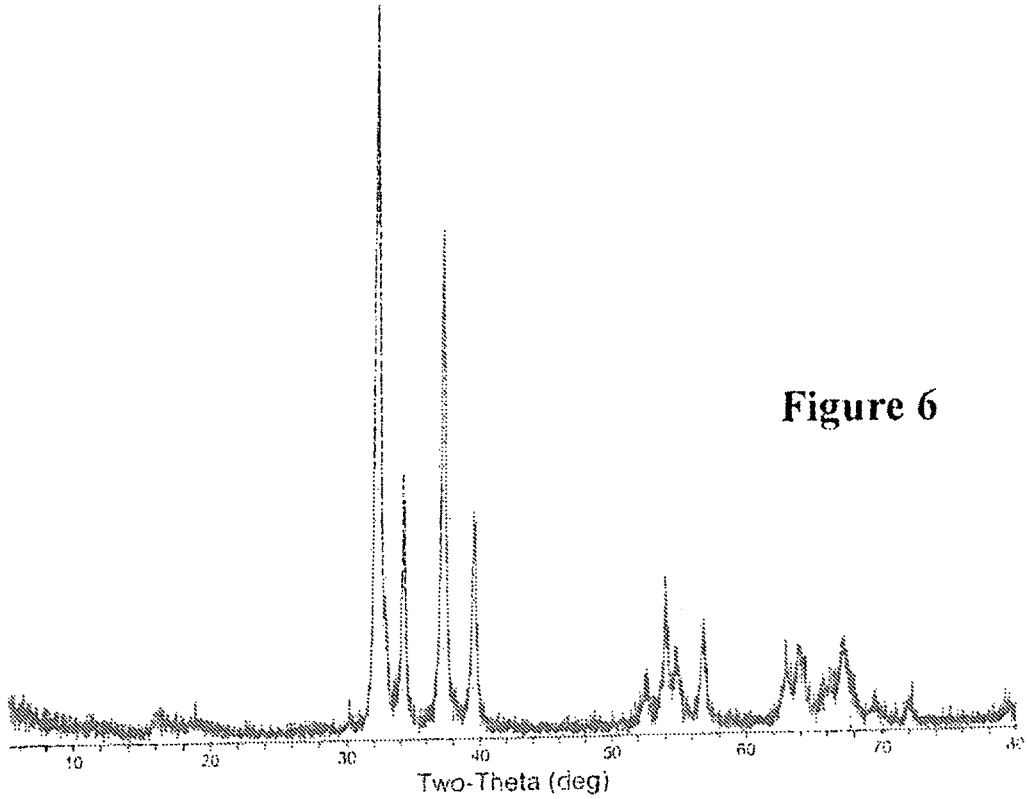
FIG. 6 is an X-ray diffraction plot of the remilled silver oxide sample associated with FIG. 3.
Figure 7:
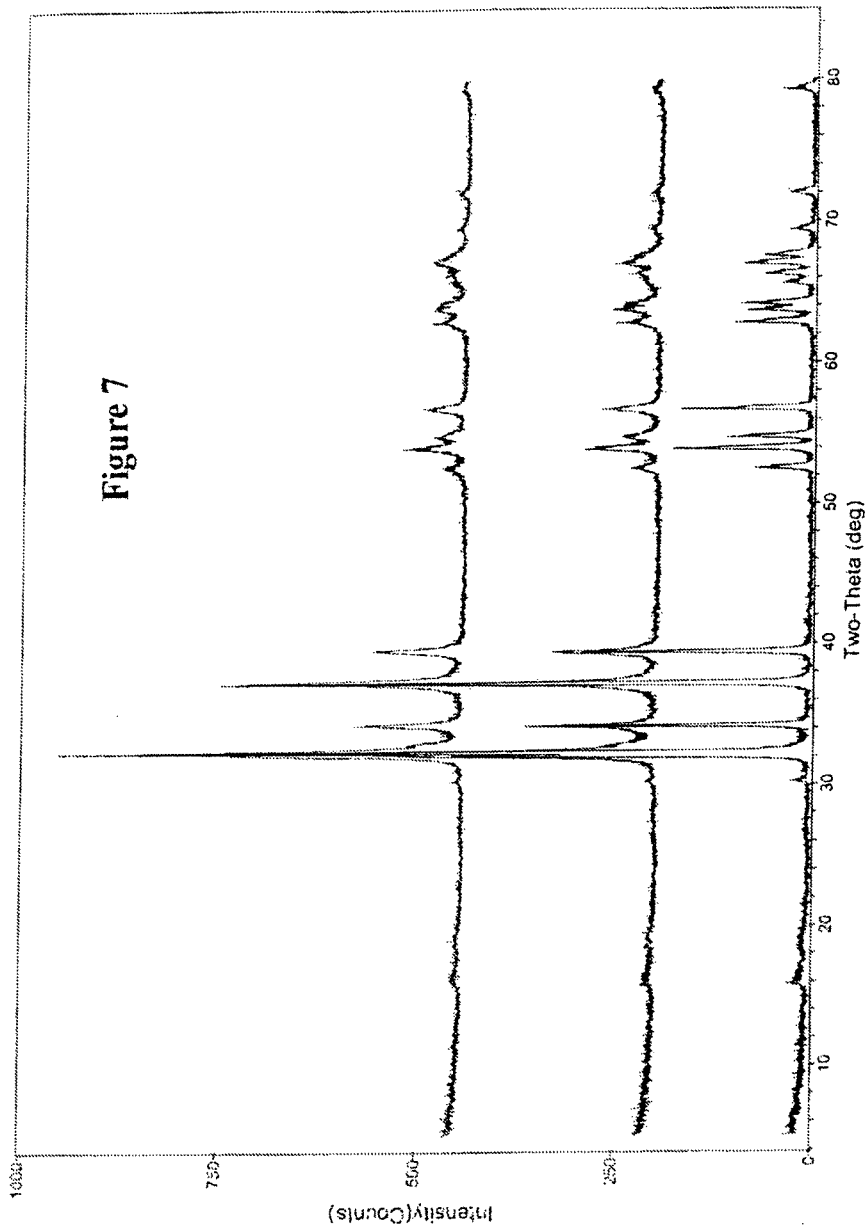
FIG. 7 is a multiple X-ray diffraction plot in which the diffraction patterns of FIGS. 4-6 are superpositioned.

The respective diffraction patterns are plotted in FIGS. 4-6 for Samples 8-10. A superposition of these diffraction patterns is provided in FIG. 7, with the diffraction pattern of Sample 8 plotted near the baseline, the diffraction pattern of Sample 9 plotted thereabove, and the diffraction pattern of Sample 10 plotted yet thereabove. Each of FIGS. 4-6 further includes a table containing detailed data obtained from the three XRD patterns.

The formation of $Ag_2O$ during milling may be observed, for example, the peak emerging at a $2\theta$ of approximately 32.8°. One may further observe a broadening of peaks, a decrease in the intensity of the diffraction lines, and slight shifts in the location of several diffraction peaks.

Without wishing to be bound by theory, we believe that some of the semi-crystalline material produced is a silver(II) oxide characterized by a low level of crystallinity. This may be supported by the broadening of various X-ray diffraction peaks associated with crystalline silver(II) oxide. For example, Tables 6-8 provide the characteristic of a given diffraction line ($2\theta$ lies between 37.1° and 37.3° in the {111} symmetry plane) appearing in both the raw material (Sample 8) and in the vortex-milled materials (Samples 9 and 10). The comparison refers to the peak heights and full width half maximums (FWHMs), as described hereinabove. Sample 8, consisting of unmilled silver oxide, yielded a FWHM of 0.190°. Vortex-milled Sample 9 which was milled from Sample 8, exhibited a broadened peak having an FWHM of 0.312°. Vortex-milled Sample 10 which was produced by remilling Sample 9, exhibited a further broadening of peak, characterized by an FWHM of 0.356°.

The net broadening, after subtracting the instrumental broadening, is 0.110 for Sample 8, and 0.232 and 0.276, respectively, for vortex-milled Samples 9 and 10, respectively.

Example 9

Material from Samples 8-10 was subjected to chemical analysis. The silver content was determined using an inductively coupled plasma (ICP) spectrometer (Varian AES Vista AX), and oxygen content was determined by means of a thermogravimetric analysis (TGA) instrument (TA Instruments, USA), under a nitrogen environment. The chemical analyses of the samples are provided in Table 6.

TABLE 6

|  | | Stage 1 | | Stage 2 | | | Total | [$Ag_2O$] |
|---|---|---|---|---|---|---|---|---|
|  | [Ag] (%) | [O] (%) | Temp. (° C.) | [O] (%) | Temp. (° C.) | (O] Total (%) | [Ag] + [O] (%) | calculated (%) |
| Sample 8 | 88.75 | 5.95; | 204.6 | 6.94; | 420.8 | 12.89 | 101.64 | 3.9 |
| Sample 9 | 89.35 | 5.78; | 197.5 | 6.93; | 421.1 | 12.71 | 102.06 | 7.7 |
| Sample 10 | 89.55 | 5.86; | 194.1 | 6.84; | 422.2 | 12.70 | 102.25 | 8.3 |

Figure 8:
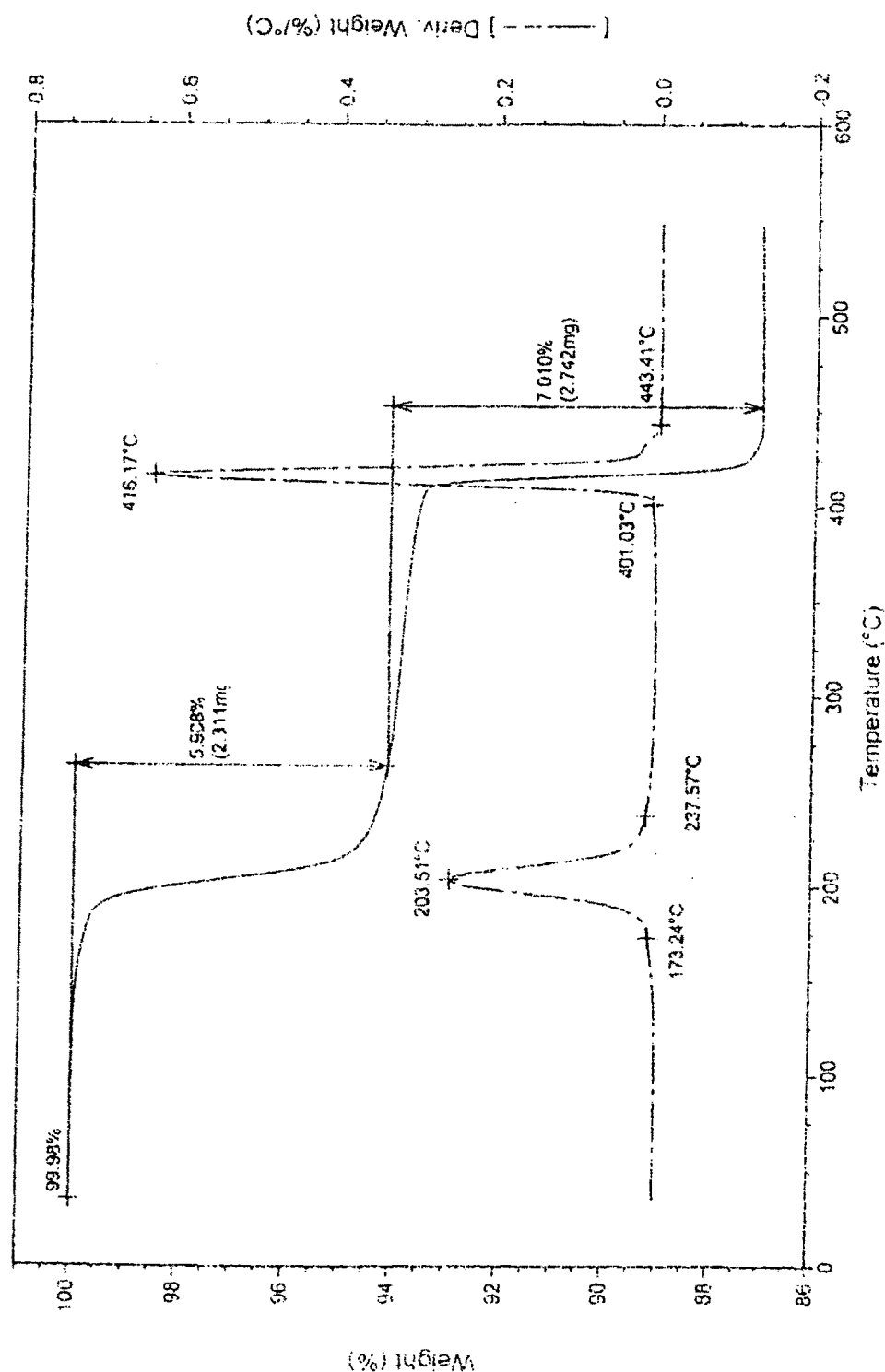
FIG. 8 is a plot of the thermogravimetric analysis (TGA) performed on the unmilled silver oxide sample associated with FIG. 1.
Figure 9:
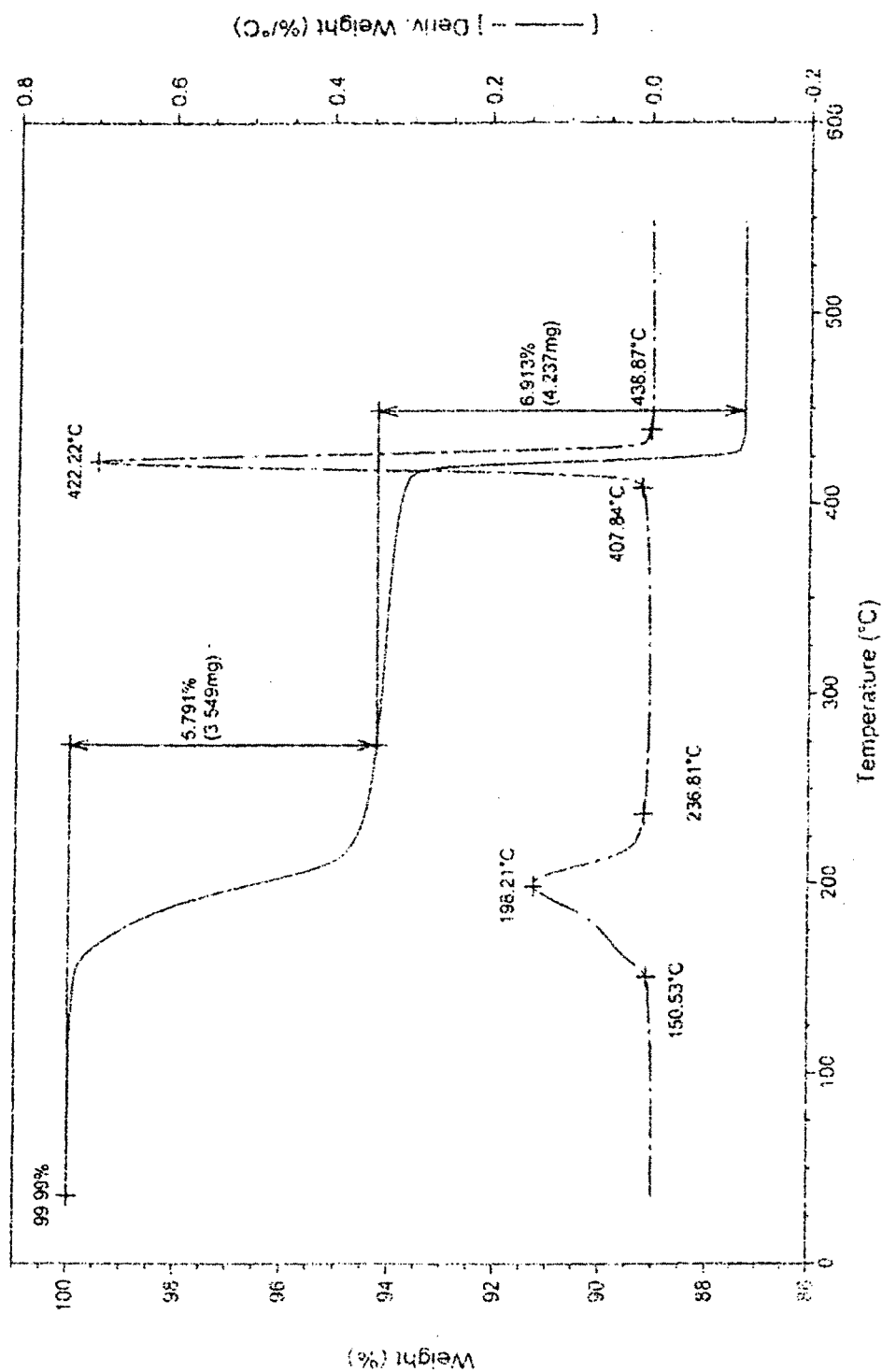
FIG. 9 is a plot of the thermogravimetric analysis (TGA) performed on the vortex-milled silver oxide sample associated with FIG. 2.
Figure 10:
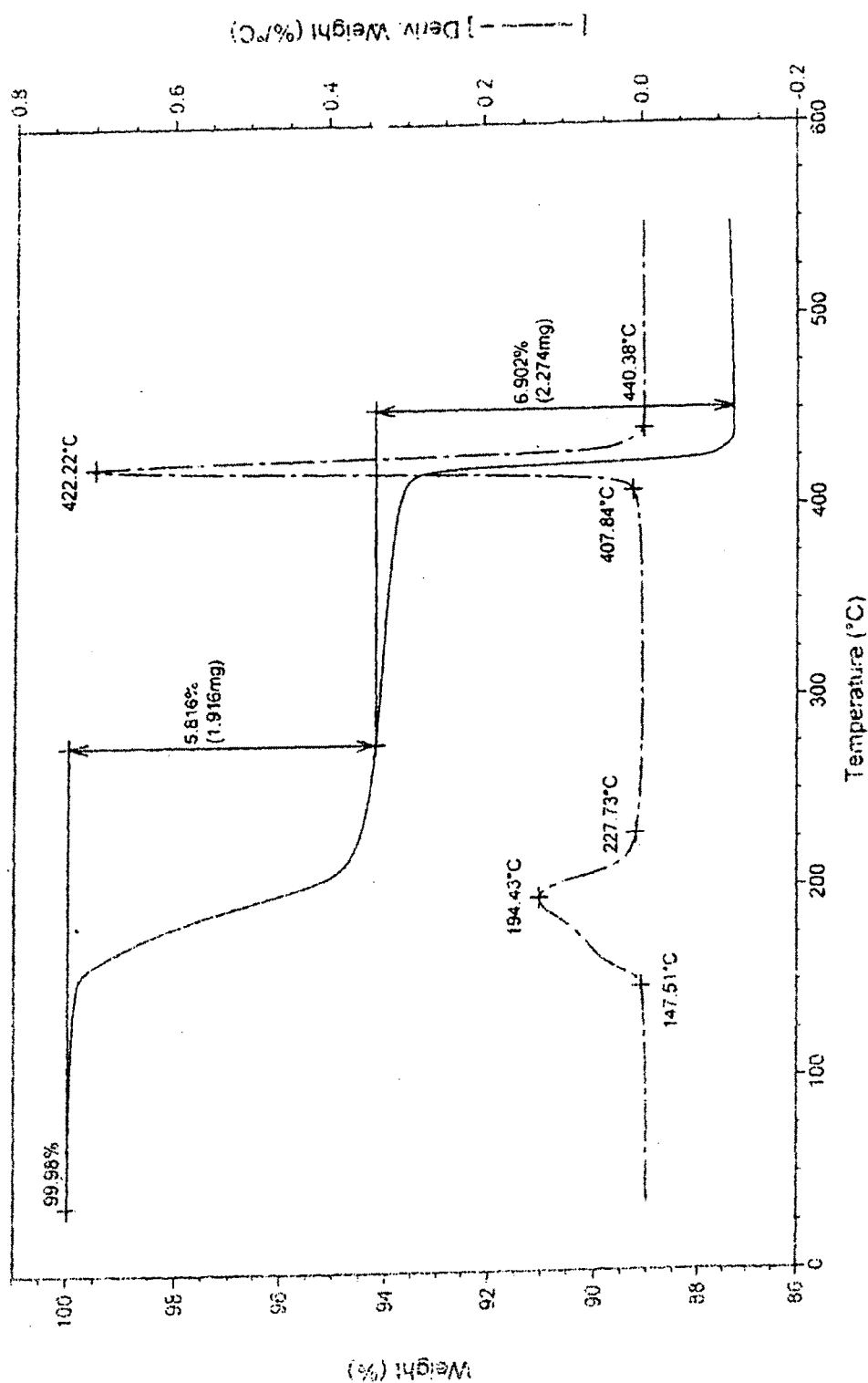
FIG. 10 is a plot of the thermogravimetric analysis (TGA) performed on the remilled silver oxide sample associated with FIG. 3.

In FIGS. 8-10, the percentage of the original sample weight is plotted as a function of temperature on the first Y-axis; the derivative of this curve ("derivative curve") is plotted on the second Y-axis. The temperature in the TGA sample chamber was ramped up from room temperature (25° C.) to about 550° C., at a rate of 10° C./minute.

The oxygen in the solid samples appears to be liberated in two distinct stages: in a first stage, around 200° C., in which the more labile oxygen is driven off, and in a second stage, around 420° C., in which the remainder is driven off.

Referring now to the first stage, and with specific reference to the derivative curve, the weight loss per unit change in temperature (dW/dT) associated with the evolution of oxygen from Sample 8 is substantially constant until 173° C. At 173° C., dW/dT begins to accelerate ("first shoulder of the derivative") at about 173° C., peaks at 204° C. (i.e., reaches a constant, maximum rate of weight loss per unit increase in temperature), and decelerates and largely concludes at 238° C. By sharp contrast, the derivative curve peak for milled Sample 9 is at 198° C., and the accelerated evolution of oxygen from Sample 9 begins at about 151° C., over 20° C. lower than the corresponding value for Sample 8. With regard to twice-milled Sample 10, the derivative curve peak is at 194° C., and the accelerated weight loss associated with the evolution of oxygen from Sample 9 begins at about 148° C., over 25° C. lower than the corresponding value for Sample 8. The differences in the respective derivative curve peak profiles (of the first stage) are particularly apparent in the graphical representations provided in FIGS. 8-10. The peak profile broadens, and loses its sharpness, with increased milling time in the vortex mill.

Without wishing to be limited by theory, we believe that the weight loss/evolution of oxygen at significantly lower temperatures may be at least partially attributed to the increased strain within the silver oxide particles, which correspondingly increases the lability of the oxygen. In any event, it is surprising that the oxygen is more easily liberated than in the raw material or in pure silver(II) oxide. The induced strain is a structural characteristic that may be at least partially responsible for the increased reactivity of the inventive material, and for the enhanced anti-microbial properties of the topical formulations according to the present invention.

We further observe that the percent weight loss of the oxygen decreases for silver oxide milled in the vortex mill, with respect to the percent weight loss of the unmilled raw material. The percent weight loss associated with Sample 10 is substantially identical to that of Sample 9, which may indicate that little additional oxygen was liberated in the second milling operation.

As used herein in the specification and in the claims section that follows, the term "2θ", with respect to X-ray diffraction, is meant to be used as understood in the art of X-ray diffraction.

With respect to θ-θ XRD analyzers in which the specimen is fixed (such as the Rigaku Dmax 2000 XRD analyzer), 2θ is meant to represent the angle of the detector with respect to the specimen.

As used herein in the specification and in the claims section that follows, the term "full width half maximum", or "FWHM" of a diffraction peak is meant to be used as understood in the art of X-ray diffraction.

Since the magnitude of the measured FWHM includes instrumental broadening, the values of FWHM as claimed include such broadening, which is estimated to be 0.08-0.10 degrees of 2θ for the Rigaku Dmax 2000 XRD analyzer used, using a silicon diffraction pattern as the baseline. Thus, as used herein in the claims section that follows, the magnitude of the FWHM includes an instrumental broadening of 0.08-0.10 degrees of 2θ.

As used herein in the specification and in the claims section that follows, the term "net full width half maximum", or "net FWHM" of a diffraction peak is meant to refer to the magnitude of the measured FWHM, less the instrumental broadening, as determined using a silicon diffraction pattern as the baseline.

As used herein in the specification and in the claims section that follows, the term "macrocrystal" and the like refers to a crystal composed of a large plurality of crystallites, and/or having a particle size of at least 0.5 micrometers, at least 0.6 micrometers, or at least 1.0 micrometers. A material is said to have a macrocrystal structure if over 90% of the material, by weight, consists of macrocrystals.

As used herein in the specification and in the claims section that follows, the term "semi-crystalline" refers to a substantially macrocrystalline material having a low level or degree of crystallinity.

In the specific case of a material containing silver (II) oxide, the term "semi-crystalline" refers to a substantially macrocrystalline material having a low level or degree of crystallinity defined by a diffraction peak in a {111} symmetry plane and having a full width half maximum (FWHM) of at least 0.24 degrees of 2θ.

As used herein in the specification and in the claims section that follows, the term "silver (II) oxide" refers to a silver oxide whose unit structure contains silver and oxygen in a substantially 1:1 molar ratio. The term "silver (II) oxide" is specifically meant to include AgO, and $Ag_4O_4$ (tetrasilver tetroxide), whose structure may be represented by $Ag_2O_3 \cdot Ag_2O$.

As used herein in the specification and in the claims section that follows, the term "average particle size", or "$D_{50}$", refers to an average particle size, by weight, as determined by a laser diffraction particle size analyzer (e.g., Mastersizer™ 2000 of Malvern Instruments, England, or the like), using standard practice.

As used herein in the specification and in the claims section that follows, the term "largely includes", with respect to a component within a composition or formulation, refers to a weight content of at least at least 30%, at least 40%, at least 50%, or at least 60%.

As used herein in the specification and in the claims section that follows, the term "predominantly includes", with respect to a component within a composition or formulation, refers to a weight content of at least at least 50%, at least 65%, at least 75%, or at least 85%.

Whenever a numerical range is indicated herein, the range is meant to include the end values of the range.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

We claim:

1. A formulation comprising at least one silver oxide including a silver(II) oxide, said at least one silver oxide having an average particle size ($D_{50}$) within a range of from above 0.8 micrometers to below 8 micrometers, said silver (II) oxide having an irregular macrocrystal structure,
   said irregular macrocrystal structure characterized by a diffraction peak in a {111} diffraction plane, said diffraction peak having at least one of the following structural properties:
   (i) a measured full width half maximum (FWHM) of at least 0.30 degrees of 2θ and not more than 0.466 degrees of 2θ; and
   (ii) a net full width half maximum (net FWHM) of at least 0.20 degrees of 2θ and not more than 0.366 degrees of 2θ;
   the formulation being a topical formulation suitable for application to skin tissue, wherein said silver oxide predominantly includes said silver(II) oxide.

2. The formulation of claim 1, wherein said silver oxide includes silver(I) oxide, and wherein a ratio of said silver(I) oxide to said silver(II) oxide is at least 0.05:1, by weight.

3. The formulation of claim 1, said average particle size ($D_{50}$) being within a range of from above 0.8 micrometers to 4.5 micrometers.

4. The formulation of claim 1, containing at least 0.05%, by weight, of said silver(II) oxide.

5. The formulation of claim 3, said average particle size ($D_{50}$) being within a range of from above 0.8 micrometers to below 3 micrometers.

6. The formulation of claim 2, wherein said base material includes a liquid wax ester.

7. The formulation of claim 6, wherein said liquid wax ester includes jojoba oil.

8. The formulation of claim 1, wherein said silver oxide includes a silver(I) oxide, and wherein said ratio of said silver(I) oxide to said silver(II) oxide is less than 5:1, by weight.

9. The formulation of claim 1, wherein said measured full width half maximum (FWHM) is at least 0.35 degrees of said 2θ.

10. The formulation of claim 1, wherein said net full width half maximum (FWHM) is at least 0.25 degrees of said 2θ.

11. The formulation of claim 1, wherein said irregular macrocrystal structure is structurally characterized by a lability pattern of a thermogravimetric analysis (TGA) performed on said solid phase in a chamber, under a pure nitrogen environment and a temperature ramp rate of 10° C./minute, and wherein a derivative of weight loss of said solid phase with respect to a temperature change in said chamber peaks at a temperature below 202° C.

12. The formulation of claim 1, wherein said irregular macrocrystal structure is structurally characterized by a lability pattern of a thermogravimetric analysis (TGA) performed on said solid phase in a chamber, under a pure nitrogen environment and a temperature ramp rate of 10° C./minute, and wherein a first shoulder of a derivative of weight loss of said solid phase with respect to a temperature change in said chamber appears below 165° C.

13. A formulation comprising a solid phase containing at least one silver oxide including a silver(II) oxide, said silver(II) oxide having an irregular macrocrystal structure, said silver oxide having an average particle size ($D_{50}$) within a range of from above 0.8 micrometers to below 8 micrometers,
   wherein said irregular macrocrystal structure is structurally characterized by a lability pattern of a thermogravimetric analysis (TGA) performed on said solid phase in a chamber, under a pure nitrogen environment and a temperature ramp rate of 10° C./minute, said lability pattern characteristic of structural properties within said irregular macrocrystal structure,
   said lability pattern having both of the following properties:
   (i) a derivative of weight loss of said solid phase with respect to a temperature change in said chamber peaks at a temperature below 202° C. and at least 194° C.; and
   (ii) a first shoulder of said derivative appears below 160° C. and at least 148° C.,
   the formulation being a topical formulation suitable for application to skin tissue, wherein said silver oxide predominantly includes said silver(II) oxide.

14. The formulation of claim 13, wherein, within said topical formulation, said silver oxide is dispersed in a base material.

15. The formulation of claim 13, wherein said first shoulder of said derivative appears below 155° C.

16. The formulation of claim 14, wherein said first shoulder of said derivative appears below 150° C.

17. A formulation comprising at least one silver oxide including a silver(II) oxide, said at least one silver oxide having an average particle size ($D_{50}$) within a range of from above 0.8 micrometers to below 8 micrometers, said silver (II) oxide having an irregular macrocrystal structure,
   said irregular macrocrystal structure characterized by a diffraction peak in a {111} diffraction plane, said diffraction peak having at least one of the following structural properties:
   (i) a measured full width half maximum (FWHM) of said peak is at least 0.30 degrees of 2θ and not more than 0.466 degrees of 2θ; and
   (ii) a net full width half maximum (net FWHM) of said peak is at least 0.20 degrees of 2θ and not more than 0.366 degrees of 2θ;
   the formulation being a topical formulation suitable for application to skin tissue, and wherein, within said topical formulation, said silver oxide is dispersed in a base material.

18. The formulation of claim 1, wherein the measured full width half maximum (FWHM) of said peak is at least 0.32 degrees of 2θ.

19. The formulation of claim 17, wherein the net full width half maximum (net FWHM) of said peak is at least 0.22 degrees of 2θ.

* * * * *